United States Patent [19]
Schönfeld

[11] Patent Number: 5,860,940
[45] Date of Patent: Jan. 19, 1999

[54] METHOD OF DETERMINING THE TRAINABILITY OF A PATIENT SUFFERING FROM INCONTINENCE

[76] Inventor: Andreas Schönfeld, Nördliche Uferstrasse 4-6, 76189 Karlsruhe, Germany

[21] Appl. No.: 899,142

[22] Filed: Jul. 23, 1997

[30] Foreign Application Priority Data

Aug. 28, 1996 [DE] Germany ......................... 296 14 895 U

[51] Int. Cl.⁶ .................................................. A61B 5/103
[52] U.S. Cl. ............................................................ 600/587
[58] Field of Search .................................. 600/546, 552, 600/554, 587, 591

[56] References Cited

U.S. PATENT DOCUMENTS

| | | | |
|---|---|---|---|
| 4,396,019 | 8/1983 | Perry, Jr. .................................. | 600/546 |
| 4,515,167 | 5/1985 | Hochman ................................. | 600/549 |
| 5,154,177 | 10/1992 | Eisman et al. .......................... | 600/546 |
| 5,291,902 | 3/1994 | Carman ................................... | 600/546 |
| 5,411,548 | 5/1995 | Carman ................................... | 600/546 |
| 5,423,329 | 6/1995 | Ergas ...................................... | 600/546 |
| 5,474,083 | 12/1995 | Church et al. .......................... | 600/546 |

*Primary Examiner*—Max Hindenburg
*Assistant Examiner*—Charles Marmor, II
*Attorney, Agent, or Firm*—Klaus J. Bach

[57] ABSTRACT

In an apparatus for determining the innervation degree of pelvis base muscles, anal sphincter muscles or pubcoccygeal muscles which includes a sensor for generating a muscle force signal, a signal processing unit receiving the signal from the sensor, and a signal indicator connected to the signal processing unit for indicating signal values, there is further provided an arrangement for detecting and displaying peak signal values which are utilized to determine whether muscle training therapy is likely to be successful.

2 Claims, 1 Drawing Sheet

METHOD OF DETERMINING THE TRAINABILITY OF A PATIENT SUFFERING FROM INCONTINENCE

BACKGROUND OF THE INVENTION

The invention relates to a method for determining the trainability of a patient suffering from incontinence by determining the innervation of the pelvis base muscles, the anal sphincter muscles or the pubococcygeal muscles and comparing the values with predetermined values.

Apparatus for the treatment of human incontinence have been devised by which the activity of the pelvis base muscles, the anal sphincter muscles or the pubococcygeal muscles can be determined. The activity of the muscles is recorded by means of an electromyogram (EMG). The forces generated by the various muscles are indicated for example by a series arrangement of light emitting diodes.

A particular person, can be motivated to increase the intensity or the activity of the respective muscles through the use of feedback coupling to that person to indicate the activity or contraction forces of the respective muscles. It is the aim of the person subjected to such training to achieve a high muscle activity for a relatively long period. With an increase of the muscle activity, the person can learn to control and finally eliminate incontinence.

DE 94 16 826U discloses an apparatus for training the closing muscles wherein a sensor is inserted into the anal canal which senses the electric potentials generated during activation of the anal sphincter muscles and transmits them to a processing unit. The sensor signal is first processed in a signal processing unit and is then transmitted to an display control unit. With the display control unit, the light emitting diodes are controlled. The sensor signal is essentially filtered in the signal processing unit. In order to obtain a flicker-free signal display, the signal is passed through a low-pass filter wherein signal valleys and peaks are equalized in order to achieve a steady display signal.

It has now been found that with such training apparatus not only the anal incontinence, but also a certain type of urinal incontinence, the so-called stress incontinence, can be improved or even eliminated. However, it has further been found that the stress incontinence can be improved or eliminated only if the innervation of the pelvis base muscles, the anal sphincter muscles or the pubococcygeal muscles is in a certain range. To determine whether the innervation of these muscles is in a certain range the apparatus known in the field are not suitable.

It is the object of the present invention to provide a method which permits a classification of the innervation degree of the muscles. The innervation degree, for example, indicates to what degree the pelvis base muscles are in communication with the nerve system.

SUMMARY OF THE INVENTION

In the method for determining the innervation degree of pelvis base muscles, anal sphincter muscles or pubococcygeal muscles wherein a muscle force signal, a signal processing unit receives the signal from the sensor, and a signal indicator connected to the signal processing unit indicates signal values, the peak signal values are compared with given values to determine whether muscle training therapy is likely to be successful.

The peak values which indicates the peak activities of the muscles occur only for short periods. These values indicate the degree of the nerve stimulation of the muscles independent of the actual force generated by the muscle activation and its duration. The peak values facilitate a determination whether the muscles can be trained that is whether incontinence can be improved with the known training apparatus.

If the peak values are below a certain first value, the muscles are already so weakened that they cannot be built up by the physical training methods which can be performed with the known training apparatus. The muscles must then first be conditioned by other means such as pharmaceutical means such that they can then be trained by the known training apparatus.

If the peak value exceeds a certain second value, the muscles are so strongly innervated that training of the muscles with the known training methods would not improve the incontinence. Then the incontinence must first also be treated by means of other methods possibly by pharmaceutical medication.

However, if the peak value is above the certain first value and below the certain second value, then there is stress incontinence which can be improved or eliminated by a training of the muscles with the known training apparatus. With the apparatus according to the invention, the therapist is in a position to determine whether the incontinence is a stress incontinence which can be improved by muscle training.

It is particularly advantageous if the apparatus includes a memory which stores the signal peak values. In this way, it is easily determined which peak values were reached by the sensor signal and, accordingly for the muscle activities or respectively, the contraction forces of the muscles.

The signal stored in the memory can be easily displayed by a digital display or it can be presented by an analog indicator such as an array of light emitting diodes. In a particular embodiment of the invention, the peak signal value is compared in a comparator with at least one predetermined value. However, preferably the peak signal value is compared with two predetermined values that is a lower value representing the certain first value and an upper value representing the certain second value of the range in which incontinence can be improved by muscle training. For adopting the apparatus to different patients the first and second values are adjustable threshold values. The output signal of the comparator can then be used as an indicator whether the muscles are too weak, whether they are in an area where they can be trained or whether the muscles are so strong that normal training would not lead to an improvement in the incontinence.

Another preferred embodiment of the invention includes a control for activating the apparatus. The control may determine the time frame in which the peak signal values are to be determined by manual operation of switches or automatically. For automatic operation, the control may be so designed that it initiates a measuring procedure at predetermined time intervals and for predetermined time periods or that the measurement procedure is initiated manually by operating a switch and is terminated by the control automatically after a certain period of time.

Further features and advantages of the invention will be described below on the basis of the accompanying drawings.

DESCRIPTION OF THE METHOD UTILIZING AN APPARATUS

Figure 1:
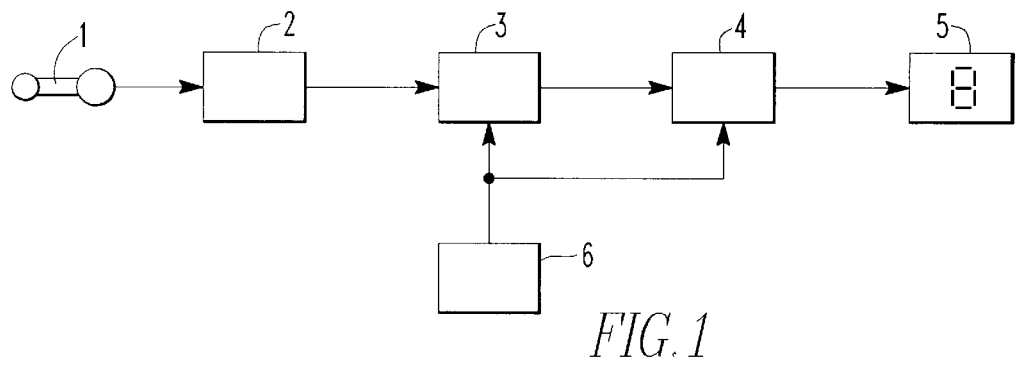
FIG. 1 shows an apparatus for determining innervation values.

The same elements are designated in the drawings by the same numerals. As shown in FIG. 1, a sensor 1, which can be inserted into an anal canal or into a vagina, is connected to a signal processing unit 2. In the signal processing unit 2 certain specific signal components are extracted from the full signal generated by the sensor 1. The signal output of the signal processing unit 2 is transmitted to an arrangement 3 for recording the peak signal values. The arrangement 3 is provided with a control device 6 by which it can be activated. The control unit 6 determines during which period of time the arrangement 3 records the peak signal values supplied by the signal processing unit 2. The arrangement 3 is also connected to the input of a memory unit 4 which stores the peak signal values recorded by the arrangement 3. The signal stored in the memory unit 4 is supplied to an indicator unit 5 which represents the signal in a numeric form. The memory unit 4 is also connected to the control unit 6 which resets the value stored in the memory unit at the beginning of a measuring cycle.

Figure 2:
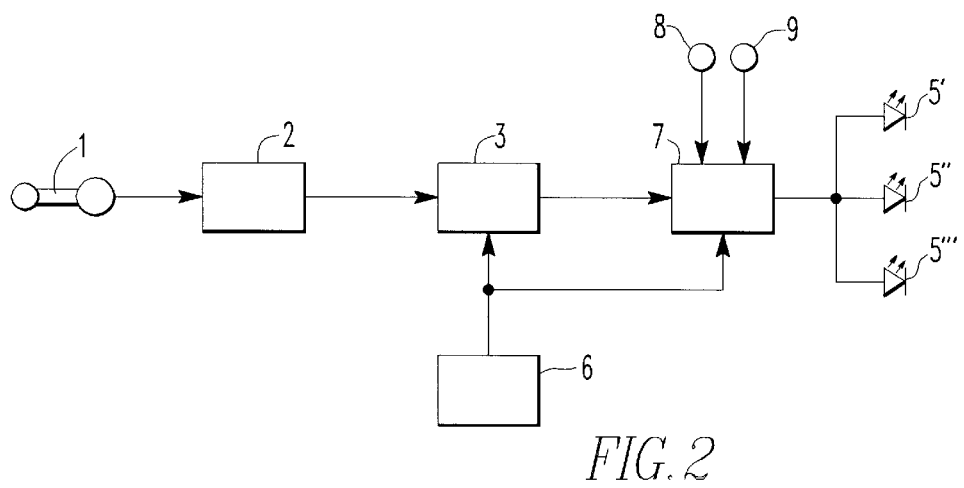
FIG. 2 shows a second embodiment of the apparatus according to the invention.

As shown in FIG. 2, instead of a memory unit 4, there may be a comparator 7 which compares the signal value recorded by the arrangement 3 with two threshold values 8, 9. The output signal of the comparator 7 is supplied to three light emitting diodes 5', 5", 5'". If the peak signal value is below the first predetermined threshold value 8, the diode 5' is lit up, indicating the muscles are already so weakened that they cannot be built up by the physical training methods which can be performed with known training apparatus. If the peak signal value is greater than the second predetermined threshold value 9, the diode 5" is lit up, indicating the muscles are so strongly innervated that training of the muscles with the known training methods would not improve incontinence. If the peak signal value is between the two threshold values 8 and 9, the diode 5'" is lit up, indicating there is stress incontinence which can be improved or eliminated by the physical training of the muscles with known training apparatus. The comparator 7 is connected to the control unit 6 which resets the output signal of the comparator 7 at the start of each new measuring cycle.

What is claimed is:

1. A method of determining trainability of a person suffering from incontinence, comprising the steps of determining the innervation degree of the pelvis base muscles, the anal sphincter muscles or the pubococcygeal muscles by determining the maximum muscle forces that can be generated, comparing the maximum muscle force that can be generated with a predetermined first, low and a second, high values and determining trainability if said determined maximum muscle force is between said first and second values and determining non-trainability if said maximum muscle force is below or above said first and second values, respectively.

2. A method according to claim 1, wherein said predetermined first and second values are stored in a memory and said maximum muscle force value that can be generated is considered to be insufficient for closing said muscles if it is below said first value and is considered to be sufficient for closing said muscles such that insufficient muscle innervation is not the reason for the incontinence if the maximum muscle force value is above said second value.

* * * * *